(12) United States Patent  
Kobayashi et al.

(10) Patent No.: US 6,747,157 B2
(45) Date of Patent: Jun. 8, 2004

(54) PROCESSES FOR THE PREPARATION OF OXO-OXAZOLINE OR ALLOAMINO ACID DERIVATIVES

(75) Inventors: Makoto Kobayashi, Hyogo (JP); Haruo Koike, Hyogo (JP); Masahiko Nagai, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 75 days.

(21) Appl. No.: 10/229,819

(22) Filed: Aug. 27, 2002

(65) Prior Publication Data

US 2003/0055264 A1 Mar. 20, 2003

Related U.S. Application Data

(62) Division of application No. 10/070,974, filed as application No. PCT/JP00/05753 on Aug. 25, 2000, now Pat. No. 6,541,641.

(30) Foreign Application Priority Data

Aug. 30, 1999 (JP) .......................................... 11-242647

(51) Int. Cl.⁷ .......................................... C07D 263/20
(52) U.S. Cl. ....................................... 548/230; 562/512
(58) Field of Search ........................... 548/230; 562/512

(56) References Cited

FOREIGN PATENT DOCUMENTS

| JP | 60-34955 | 2/1985 | ......... C07D/263/24 |
|---|---|---|---|
| WO | WO 98/08867 | 3/1998 | |

OTHER PUBLICATIONS

C.–N. Hsiao et al., "Synthesis of N–(Tert–Butoxycarbonyl)–3–(4–Thiazolyl)–L–Alanine," *Synth. Commun.*, 20(22), pp. 3507–3517 (1990).
T. Inui, "Selective Cleavage of Cysteine Peptides," *Bull. Chem. Soc. Japan*, 44, pp. 2515–2520 (1971).
S. Kano et al., "Highly Diastereoselective Synthesis of (3R, 4R)– And (3S, 4S)–β,γ–Diamino Acids From D–Phenylalanine," *Chem. Pharm. Bull.*, 36, pp. 3341–3347 (1988).
S. Kano et al., "A New Facile Diastereoconversion of 2–Amino Alcohols Involving A Novel Cyclocarbamation," *Tet. Lett.*, 28, pp. 6331–6334 (1987).
S. Kano et al., "Diastereoconversion Of Threo 2–Amino Alcohols To Erythro Isomers Through A New Cyclocarbamation," *Heterocycles*, 27, 1241–1248 (1988).
T. Nishi et al., "Syntheses and Biological Activities of Renin Inhibitors Containing Statine Analogues," *Chem. Pharm. Bull.*, 38(1), pp. 103–109 (1990).
L.A. Paquette et al., "Asymmetric Induction in the Sulfene–Enamine Condensation Reaction: The Transition State Geometry of Such (2+2) Cycloadditions," *Tetrahedron*, 27, pp. 2599–2607 (1971).
A. Saeed and D.W. Young, "Synthesis of L–β–Hydroxyaminoacids Using Serine Hydroxymethyltransferase," *Tetrahedron*, 48(12), pp. 2507–2514 (1992).
*Heterocycl. Commun.*, 2(1), 55–56 (1996).
*Tetrahedron: Asymmetry*, 8(2), 231–243 (1997).

*Primary Examiner*—Joseph K. McKane
*Assistant Examiner*—Kamal Saeed
(74) *Attorney, Agent, or Firm*—Fish & Neave

(57) ABSTRACT

A method for producing a compound represented by the general formula (I-A) or the general formula (I-B), comprising the following step:

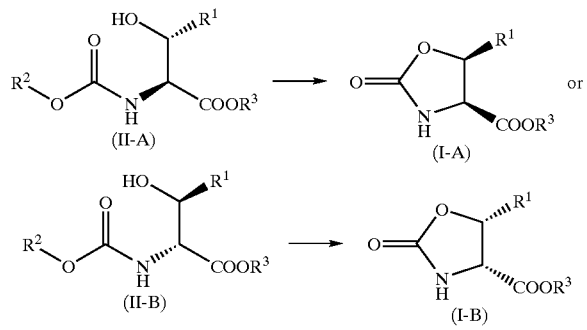

wherein $R^1$ is an optionally substituted lower alkyl, and the like; $R^2$ is a lower alkyl or an optionally substituted aralkyl, and the like; $R^3$ is a lower alkyl, characterized in that a compound represented by the general formula (II-A) or the general formula (II-B) is treated with thionyl chloride.

1 Claim, No Drawings

PROCESSES FOR THE PREPARATION OF OXO-OXAZOLINE OR ALLOAMINO ACID DERIVATIVES

This is a division of U.S. application Ser. No. 10/070,974, filed Jun. 19, 2002, now U.S. Pat. No. 6,541,641 which is a 35 U.S.C. § 371 National Stage application of International Application PCT/JP00/05753, filed Aug. 25, 2000, which designates the United States of America and was published under PCT Article 21(2) in Japanese.

TECHNICAL FIELD

The present invention relates to a method for producing oxo-oxazoline derivatives using a simple and inexpensive method.

BACKGROUND ART

Oxo-oxazoline derivatives are critical intermediates for compounds (WO98/08867) which are TRH (thyrotropin releasing hormone) derivatives represented by the following general formula (VIII):

(VIII)

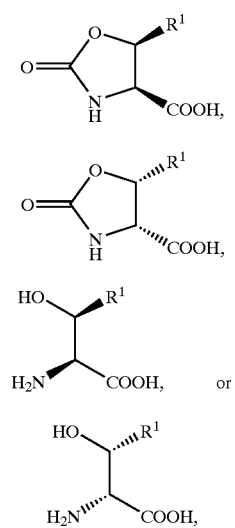

wherein $R^A$ is a hydrogen atom or optionally substituted lower alkyl; Y is an optionally substituted alkyl.

Further, compounds represented by the following general formulas (III-A), (III-B), (IV-A), or (IV-B):

(III-A)

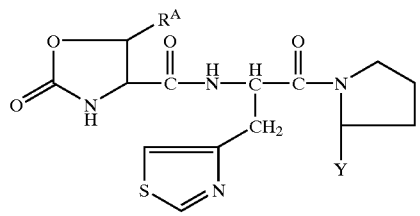

(III-B)

(IV-A)

or (IV-B)

wherein $R^1$ is an optionally substituted lower alkyl, an optionally substituted aryl, an alkynyl, or an optionally substituted heteroaryl, and derivatives thereof, are useful as tools for combinatorial chemistry.

Conventionally, as a method for producing oxo-oxazoline derivatives having a lower alkyloxycarbonyl group or a carboxyl group, a method of cyclizing a starting material while retaining its stereochemistry, and a method using cyclization reaction without reference to stereoselectivity are known.

An example of the method of cyclizing a starting material while retaining its stereochemistry is the following:

(Tetrahedron, 48, 2507, 1992). In this reaction, L-allo-threonine used as a starting material is allowed to react with phosgene and potassium hydroxide in toluene at 0° C. for one hour, thereby obtaining a cyclized product which retains its stereochemisty. Unfortunately, this method encounters a problem in industrialization since the method employs L-allo-threonine which is more expensive than its natural type, and phosgene which is toxic to the human body.

An example of the cyclization method without reference to stereoselectivity is the following:

(Japanese Laid-Open Publication No. 60-34955). In this reaction, a starting material is allowed to react with potassium carbonate in water at 60° C. for 1.5 hours to obtain a cyclized product. It is believed that the stereochemistry of the material is maintained in view of the mechanism of this method. Therefore, it is considered that allo-threonine needs to be used as a starting material in order to obtain a cis-form cyclized product.

Although a resultant cyclized product is an oxo-oxazoline derivative which does not have a lower alkyloxycarbonyl group or a carboxyl group, the following method is known:

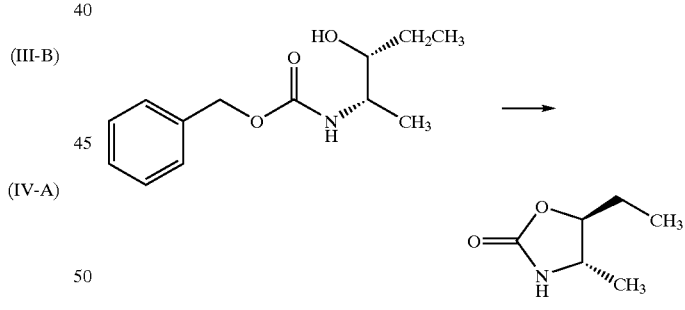

(Bull. Chem. Soc. Japan., 44, 2515, 1971). In this reaction, a starting material is allowed to react in thionyl chloride at 60° C. for 24 hours without solvent, thereby obtaining a cyclized product at a yield of 65%. In this method, similar to the method of the present invention, the position of an ethyl group is inverted after the reaction. However, the starting material is not an amino acid derivative, and the relationship between the amino group and the hydroxyl group of the starting material is different from that of a starting material used in the method of the present invention. Moreover, since the reaction is conducted in thionyl chloride, the yield is as low as 65%.

Similar to the method of the present invention, a cyclization reaction with inversion is known:

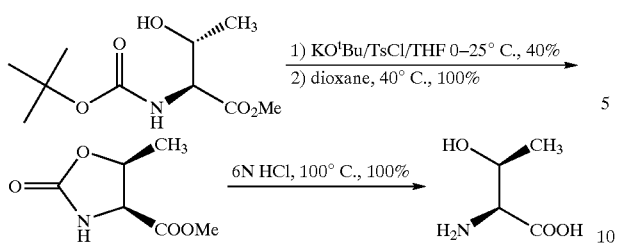

(Heterocycl. Commun., 2, 55, 1996). An example in which trifluoroacetic anydride is used in the first step is disclosed. Although in the method of the present invention, the yield of a cyclization reaction is as high as 83%, the yield of the cyclization reaction disclosed in the above-described publication is as low as 40% in both a method using tosyl chloride and a method using trifluoroacetic anydride. Moreover, the method of the present invention is superior in regard to simplicity of reaction.

DISCLOSURE OF THE INVENTION

The objective of the present invention is to provide a method for producing oxo-oxazoline derivatives in a simple, inexpensive and stereoselective manner. The oxo-oxazoline derivatives are useful as intermediates for pharmaceuticals and tools for combinatorial chemistry. Moreover, the oxo-oxazoline derivatives in an open-circular form are also useful as tools for combinatorial chemistry.

The inventors found a method for producing oxo-oxazoline derivatives in a stereoselective manner, which is suitable for large-scale synthesis.

That is, the present invention relates to

I) A method for the production of a compound represented by a general formula (I-A) or a general formula (I-B), comprising the step of treating a compound represented by a general formula (II-A) or a general formula (II-B) with thionyl chloride as follows:

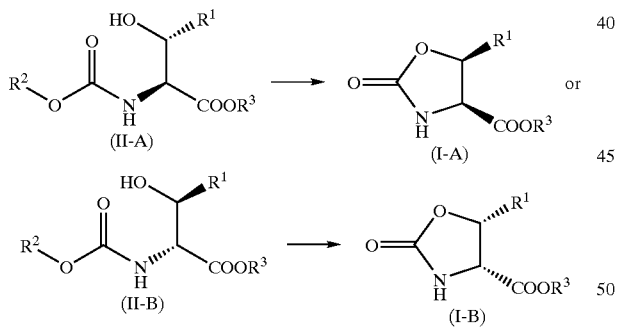

wherein $R^1$ is an optionally substituted lower alkyl, an optionally substituted aryl, an alkynyl, or an optionally substituted heteroaryl; $R^2$ is a lower alkyl, an optionally substituted aralkyl, or an optionally substituted heteroarylalkyl; and $R^3$ is a lower alkyl.

More specifically, the present invention relates to following II) to X).

II) A method for the production according to I), wherein the compound represented by the general formula (II-A) or the general formula (II-B) is allowed to react with 1.0 to 5.0 equivalents of thionyl chloride in a solvent of toluene, ethyl acetate, cyclohexane, or acetonitrile at 30° C. to reflux temperature.

III) A method for the production according to I), wherein the compound represented by the general formula (II-A) or the general formula (II-B) is allowed to react with 1.0 to 3.0 equivalents of thionyl chloride in a solvent of toluene, ethyl acetate, cyclohexane, or acetonitrile at 60° C. to 80° C.

IV) A method for the production of a compound represented by a general formula (III-A) or a general formula (III-B), comprising the step of subjecting a compound represented by a general formula (I-A) or a general formula (I-B) obtained by a method according to any of I) to III) to a hydrolysis as follows:

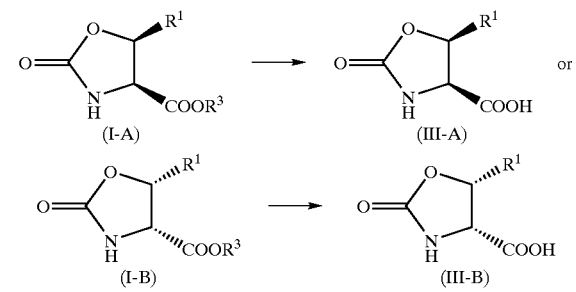

wherein $R^1$ and $R^3$ are as described above.

V) A method for the production of a compound represented by a general formula (IV-A) or a general formula (IV-B), comprising the step of subjecting a compound represented by a general formula (III-A) or a general formula (III-B) obtained by a method according to IV) to a hydrolysis as follows:

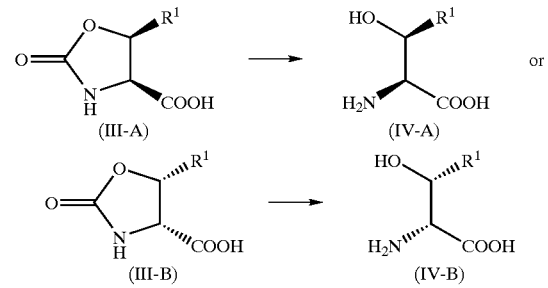

wherein $R^1$ is as described above.

VI) A method for the production of a compound represented by a general formula (I-A) or a general formula (I-B), comprising the step of protecting the amino group of a compound represented by a general formula (V-A) or a general formula (V-B) with $R^2OC(=O)$—, wherein $R^2$ is as described above, esterifying the carboxyl group thereof, and treating with thionyl chloride as follows:

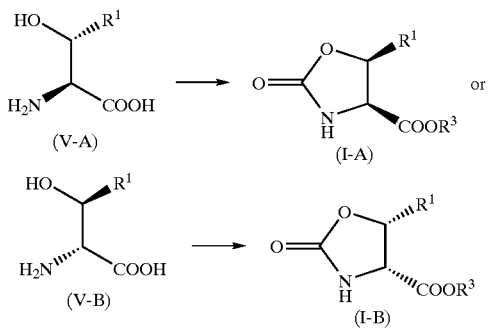

wherein $R^1$ and $R^3$ are as described above.

VII) A method for production of a compound represented by a general formula (VI):

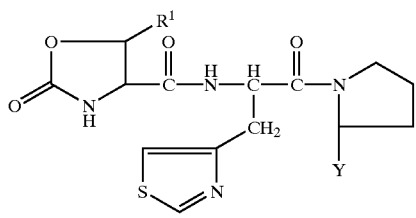

(VI)

wherein R¹ is as described above, and Y is an optionally substituted alkyl, comprising the step of subjecting a compound represented by a general formula (III-A) or a general formula (III-B) obtained by a method according to IV) to a peptide bond formation.

VIII) A method for the production according to IV), wherein R¹ is phenyl, 5-imidazolyl, methyl, isopropyl, ethynyl, or 1-propynyl.

IX) A method for the production according to IV), wherein R² is a lower alkyl, an aralkyl, or a heteroarylalkyl.

X) A method for the production according to IV), wherein R² is an aralkyl.

XI) A method for the production according to IV), wherein R¹ is methyl and R² is benzyl.

"Halogen" as used herein refers to fluorine, chlorine, bromine, and iodine. Chlorine and bromine are preferable.

The term "lower alkyl" as herein used alone or in combination with other words comprises $C_1$–$C_6$ straight chained or branched alkyl. Examples of the lower alkyl include methyl, ethyl, n-propyl, isopropyl, n-butyl, sec-butyl, isobutyl, and t-butyl, and the like. Methyl and ethyl are preferable.

"Alkynyl" as used herein comprises $C_2$–$C_8$ straight or branched chain monovalent hydrocarbon group having one or two or more triple bonds. The alkynyl may have a double bond. Examples of the alkynyl include ethynyl, 1-propynyl, 2-propynyl, 6-heptynyl, 7-octynyl, and 8-nonyl, and the like. Ethynyl and 1-propynyl are preferable.

The term "aryl" as herein used alone or in combination with other words comprises a monocyclic or condensed ring aromatic hydrocarbon. Examples of the aryl include phenyl, 1-naphthyl, 2-naphthyl, anthryl, and the like.

"Aralkyl" as used herein comprises the above-described "lower alkyl" substituted with the above-described "aryl", where the substitution may be carried out at any possible position. Examples of the aralkyl include benzyl, phenylethyl (e.g., 2-phenylethyl, and the like), phenylpropyl (e.g., 3-phenylpropyl, and the like), naphthylmethyl (e.g., 1-naphthylmethyl, 2-naphthylmethyl, and the like), and anthrylmethyl (e.g., 9-anthrylmethyl, and the like), and the like. Benzyl, and the like are preferable.

"Heteroaryl" as used herein comprises a 5 to 6-membered aromatic ring including one or more atoms arbitrarily selected from oxygen atom, sulfur atom or nitrogen atom within the ring. Heteroaryl may be fused with cycloalkyl, aryl, or other heteroaryl at any possible position. Regardless whether the heteroaryl is monocyclic or fused cyclic, the heteroaryl can bind at any possible position.

Examples of the heteroaryl include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 4-imidazolyl, 5-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (e.g., 2-isoindolyl), indolyl (e.g., 1-indolyl, 2-indolyl, 3-indolyl), indazolyl (e.g., 3-indazolyl), purinyl (e.g., 8-purinyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), and benzothienyl (e.g., 2-benzothienyl). As "heteroaryl" of R¹, imidazolyl and the like are preferable.

"Heteroarylalkyl" as used herein comprises the above-described "lower alkyl" substituted with the above-described "heteroaryl", where such a substitution may be carried out at any possible position.

"Optionally substituted lower alkyl" at R¹ as used herein comprises the above-described "lower alkyl" which may have one or more substituents at any possible positions, such as hydroxy, alkyloxy (e.g., methoxy and ethoxy), mercapto, alkylthio (e.g., methylthio), cycloalkyl (e.g., cyclopropyl, cyclobutyl, cyclopentyl, cyclohexyl), halogen (e.g., fluorine, chlorine, bromine, and iodine), alkyloxycarbonyl (e.g., methyloxycarbonyl and ethyloxycarbonyl), aryloxycarbonyl (e.g., phenyloxycarbonyl), nitro, cyano, aryloxy, acyloxy, acyloxycarbonyl, alkylcarbonyl, and the like. Preferable examples of the substituent include lower alkyloxy, halogen, and the like. Examples of the "optionally substituted lower alkyl" include methyl, ethyl, n-propyl, iso-propyl, n-butyl, iso-butyl, sec-butyl, tert-butyl, and trifluoromethyl, and the like. An unsubstituted lower alkyl is preferable.

"Optionally substituted alkyl" at Y as used herein comprises the above-described "alkyl" which may have one or more substituents at any possible positions, such as hydroxy, alkyloxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluorine, chlorine, bromine, and iodine), carboxy, carbamoyl, alkyloxycarbonyl (e.g., methoxycarbonyl and ethoxycarbonyl), aryloxycarbonyl (e.g., phenyloxycarbonyl), nitro, cyano, $SO_pR^A$ (p is an integer of 1 to 3, $R^A$ is hydrogen or alkyl), $PO(OH)_2$ or P(O)OH which may be substituted with alkyl, substituted or unsubstituted amino (e.g., methylamino, dimethyl amino, and carbamoyl amino), optionally substituted aryl (e.g., phenyl and tolyl), optionally substituted heteroaryl, optionally substituted nonaromatic heterocyclic group, aryloxy, acyloxy, acyloxycarbonyl, alkylcarbonyl, nonaromatic heterocyclic carbonyl, heterocyclic imino, hydrazino, hydroxyamino, alkyloxyamino, formyl, and the like. Examples of the "optionally substituted alkyl" include methyl, ethyl, n-propyl, iso-propyl, n-butyl, iso-butyl, sec-butyl, tert-butyl, cyclopropyl, cyclopentyl, cyclohexyl, benzyl, hydroxymethyl, tert-butylcarbonyloxymethyl, morpholinomethyl, piperidinomethyl, N-methyl-1-piperazinylmethyl, ethylcarbonylmethyl, and morpholinocarbonylmethyl, acetyloxymethyl, and the like. An unsubstituted alkyl is preferable, particularly methyl.

"Optionally substituted aryl" as used herein comprises the above-described "aryl" which may have one or more substituents at any possible positions, such as hydroxy, alkyloxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluorine, chlorine, bromine, and iodine), alkyloxycarbonyl (e.g., methyloxycarbonyl and ethyloxycarbonyl), aryloxycarbonyl (e.g., phenyloxycarbonyl), nitro, cyano, aryloxy, acyloxy, acyloxycarbonyl, alkylcarbonyl, and the like. Preferable examples of the substituent include lower alkyloxy and halogen, and the like. Examples of the "optionally substituted aryl" include phenyl, 2-chlorophenyl, 3-chlorophenyl, 4-chlorophenyl, and the like. An unsubstituted aryl is preferable.

"Optionally substituted heteroaryl" as used herein comprises the above-described "heteroaryl" which may have one or more substituents at any possible positions, such as hydroxy, alkyloxy (e.g., methoxy and ethoxy), mercapto, alkylthio (e.g., methylthio), cycloalkyl (e.g., cyclopropyl, cyclobutyl, cyclopentyl, cyclohexyl), halogen (e.g., fluorine, chlorine, bromine, and iodine), alkyloxycarbonyl (e.g., methyloxycarbonyl and ethyloxycarbonyl), aryloxycarbonyl (e.g., phenyloxycarbonyl), nitro, cyano, aryloxy, acyloxy, acyloxycarbonyl, alkylcarbonyl, and the like. Preferable examples of the substituents include lower alkyloxy, halogen, and the like. Examples of the "optionally substituted heteroaryl" include 2-chloroimidazole-5-yl, 4-chloroimidazole-5-yl, and the like. An unsubstituted heteroaryl is preferable.

"Optionally substituted aralkyl" as used herein comprises the above-described "aralkyl" which may have one or more substituents at any possible positions, such as hydroxy, alkyloxy (e.g., methoxy and ethoxy), mercapto, alkylthio (e.g., methylthio), cycloalkyl (e.g., cyclopropyl, cyclobutyl, cyclopentyl and cyclohexyl), halogen (e.g., fluorine, chlorine, bromine, and iodine), alkyloxycarbonyl (e.g., methyloxycarbonyl and ethyloxycarbonyl), aryloxycarbonyl (e.g., phenyloxycarbonyl), nitro, cyano, aryloxy, acyloxy, acyloxycarbonyl, alkylcarbonyl, and the like. Preferable examples of the substituents include lower alkyloxy, halogen, and the like. Examples of the "optionally substituted aralkyl" include furyl, thienyl, pyridyl, 5-chlorofuryl, 5-thienyl, 3-chloropyridyl, and the like. An unsubstituted aralkyl is preferable.

BEST MODE FOR CARRYING OUT THE INVENTION

The production method of the present invention will be described in detail in which a starting material is one optically active substance. When the other material is used, similar reactions can be carried out. When a starting material has a substituent which is an obstacle to a reaction in first to sixth steps shown below, the starting material may be protected in advance in accordance with a method described in Protective Groups in Organic Synthesis, Theodora W Green (John Wiley & Sons), and the like, and deprotected in an appropriate stage.

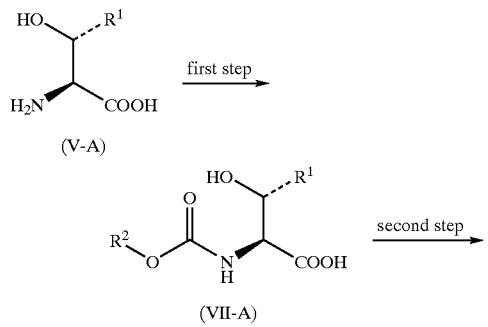

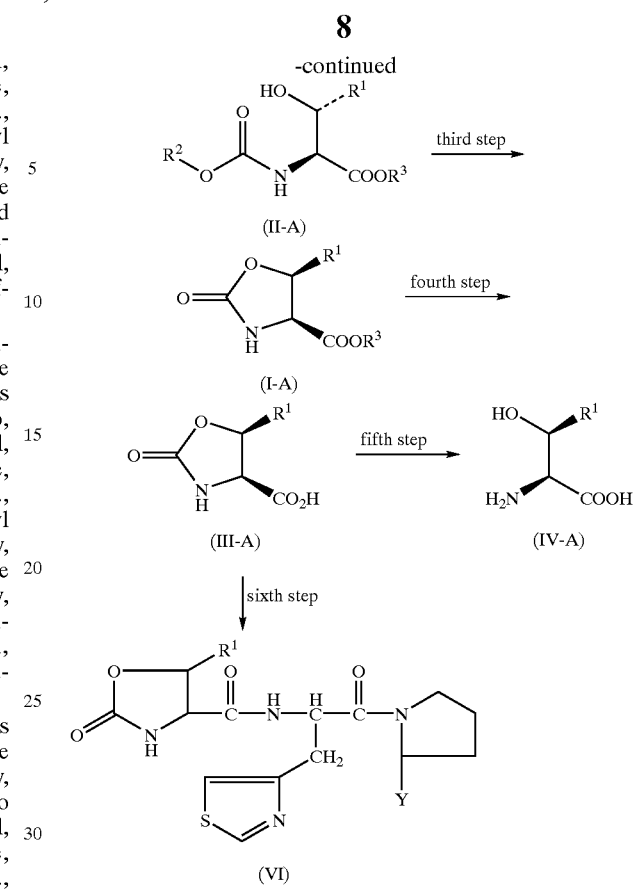

wherein $R^1$, $R^2$, $R^3$, and Y are as described above.

First Step

In the first step, $R^2OC(=O)$—Hal, wherein Hal is halogen, $[R^2OC(=O)]_2O$, and the like are caused to react with a compound represented by a general formula (V-A) to obtain a compound (VII-A) in which an amino group is protected by $R^2OC(=O)$—. This step can be carried out in accordance with a method described in Protective Groups in Organic Synthesis, Theodora W Green (John Wiley & Sons), and the like.

For example, a compound represented by a general formula (V-A) is caused to react with 1.0 equivalent to 3.0 equivalents, preferably 1.0 equivalent to 1.5 equivalents, of $R^2OC(=O)$—Hal, wherein Hal is halogen, and 2.0 equivalents to 6.0 equivalents, preferably 2.0 equivalents to 3.0 equivalents, of an organic base (e.g., triethylamine, and the like) or an inorganic base (e.g., sodium hydroxide, potassium hydroxide, sodium carbonate, potassium carbonate, sodium hydrogencarbonate, potassium hydrogencarbonate, and the like), in a mixed solvent, such as water-toluene, water-dioxane, water-acetone, and the like, or a solvent, such as water, dioxane, and the like at −20° C. to 50° C., preferably 0° C. to 20° C. for 0.5 to 3 hours to obtain a compound represented by a general formula (VII-A).

In the above-described IV), "step of protecting an amino group with $R_2OC(=O)$—" refers to this first step.

Second Step

In the second step, the carboxyl group of a compound represented by a general formula (VII-A) is esterified to obtain a compound represented by a general formula (II-A). This step can be carried out by a commonly used esterification.

For example, a compound represented by the general formula (VII-A) is dissolved in a solvent, such as methanol, ethanol, isopropyl alcohol, and the like, and allowed to react with 1 equivalent to 5 equivalents, preferably 1 equivalent to 2 equivalents, of a halogenating agent, such as thionyl chloride, hydrochloric acid, phosphorus oxychloride, and the like, at −20° C. to 50° C., preferably 0° C. to 25° C., one hour to 24 hours, preferably one hour to 3 hours to obtain a compound represented by a general formula (II-A).

In the above-described IV), "step of esterifying a carboxyl group" refers to this second step.

Third Step

The third step is a cyclization reaction in which the stereochemistry of $R^1$ is reversed.

For example, a compound represented by a general formula (I-A) can be obtained in accordance with 1) to 3) described below. 1) a compound represented by a general formula (II-A) is dissolved in a solvent, such as toluene, ethyl acetate, cyclohexane, acetonitrile, and the like, preferably toluene. The amount of the solvent is preferably 1 V to 50 V, particularly 1 V to 10 V, where use of 1 ml of a solvent with respect to 1 g of a starting material is referred to as 1 V. 2) 1.0 equivalent to 20 equivalents, preferably 1.0 equivalent to 2.0 equivalents, of thionyl chloride are added at 25° C. to 80° C., preferably 25° C. to 50° C. Thionyl chloride can be used as a solvent. 3) The reaction solution is stirred at 25° C. to 80° C., preferably 60° C. to 80° C., for 5 hours to 48 hours, preferably 6 hours to 12 hours.

In this reaction, the closer the equivalent value of thionyl chloride is to 1.0 and the higher the "V" value of the amount of the solvent, the proportion of the cis-form of the intended compound was increased (the proportion of the trans-form was decreased).

The yield of the total compounds of cis-form and trans-form is not substantially affected by the equivalent value of thionyl chloride and the amount of the solvent.

In the above-described IV), "step of treating with thionyl chloride" refers to this third step.

Fourth Step

In the fourth step, an ester compound represented by the general formula (I-A) is hydrolyzed to carboxylic acid. This step can be carried out by a commonly used hydrolysis.

For example, a compound represented by the general formula (I-A) is dissolved in a solvent, such as water, and the like, and 0.1 equivalent to 10 equivalents, preferably 1 equivalent to 5 equivalents, of acid (e.g., hydrochloric acid, sulfuric acid, and the like) are added to the solution at 0° C. to 100° C., preferably 25° C. to 80° C. The resultant solution is allowed to react at 25° C. to 100° C., preferably 50° C. to 80° C. for 1 hour to 5 hours to obtain a compound represented by a general formula (III-A). This step can be carried out under basic conditions.

Fifth Step

In the fifth step, a compound represented by the general formula (III-A) is hydrolyzed to obtain allo-amino acid derivatives represented by a general formula (IV-A).

For example, a compound represented by the general formula (III-A) is dissolved in a solvent, such as water, and 0.1 equivalent to 20 equivalents, preferably 1 equivalent to 10 equivalents, of acid (e.g., hydrochloric acid, sulfuric acid, and the like) are added to the solution at 0° C. to 100° C., preferably 25° C. to 80° C. The resultant solution is allowed to react at 25° C. to 100° C., preferably 80° C. to 100° C. for 1 hour to 48 hours to obtain a compound represented by the general formula (IV-A).

Sixth Step (Peptide Bond Formation)

Three amino acid derivatives are subjected to two peptide bond formation to synthesize a compound (VI) (WO98/08867). A compound represented by the general formula (I-A) obtained by the above-described method is used to synthesize the compound (VI) in the following two methods (method A and method B).

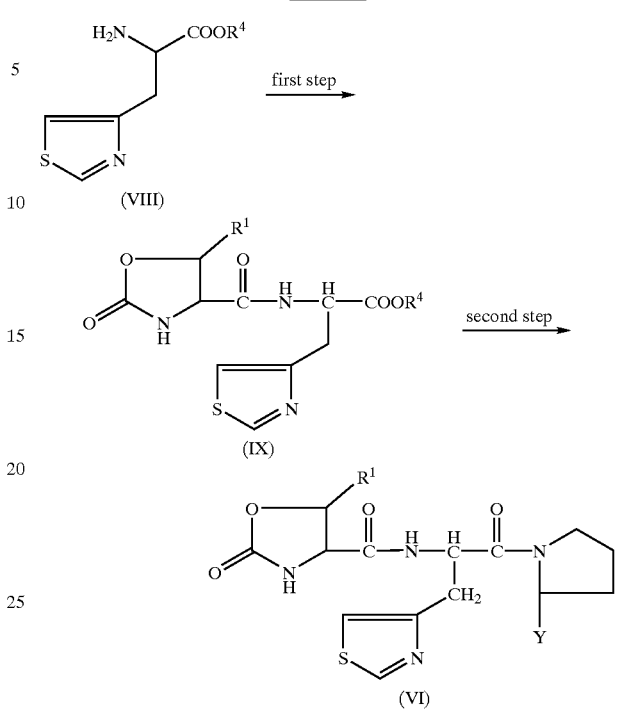

Method A

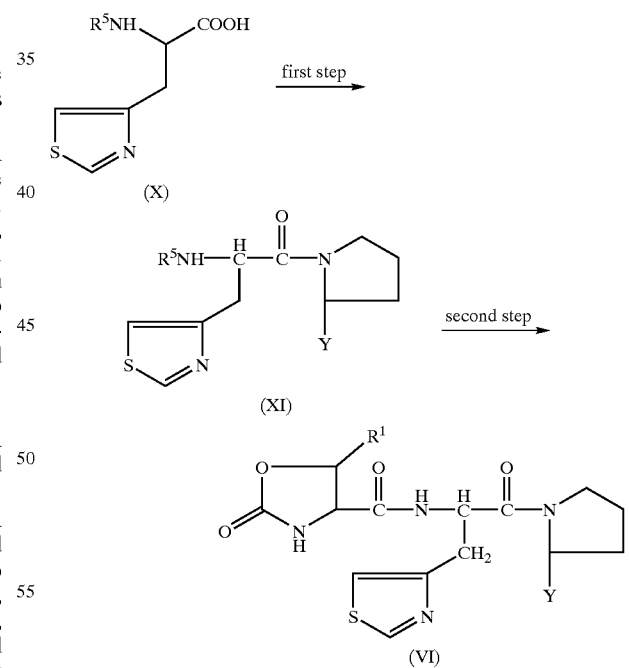

Method B wherein $R^4$ is the protecting group of a carboxyl group, $R^5$ is the protecting group of an amino group, and $R^1$ and Y are as described above.

Method A—First Step

The carboxyl group of 3-(4-thiazole)alanine synthesized in accordance with a method described in Synth. Commun., 20, 22, 3507 (1990) and Chem. Pharm. Bull., 38, 1, 103 (1990), is protected as an ester, such as methyl ester, benzyl ester, t-butyl ester, diphenylmethyl ester, and the like, resulting in a compound represented by a general formula (VIII). This compound and a compound represented by the general formula (III-A) are subjected to a peptide bond formation.

When the carboxyl group is protected as diphenylmethyl ester, the protecting reaction can be carried out as follows. 3-(4-thiazole)alanine is dissolved in a mixed solvent of an alcohol solvent, such as methanol, ethanol, and the like and a solvent, such as tetrahydrofuran, dioxane, and the like. 1 to 3 equivalents, preferably 1 to 2 equivalents, of diphenyl diazomethane are added to the solution at 0 to 50° C., preferably 20 to 40° C. for 10 minutes to 1 hour, preferably 20 to 40 minutes. The resultant solution is allowed to react at the same temperature for 30 minutes to 3 hours, preferably 1 to 2 hours while being stirred.

The peptide bond formation is described in "Peptide Gosei [Peptide Synthesis]" (Nobuo Izumiya, Maruzen), and the like, and can be carried out by such a commonly used peptide bond formation method.

As commonly used peptide bond formation methods, a method employing a condensing agent, such as N,N-dicyclohexylcarbodiimide (DCC), and the like, an azide method, an acid chloride method, an acid anhydride method, an active ester method, and the like. When a starting material has a substituent (amino, carboxy, hydroxyl, and the like) which is an obstacle to the peptide formation, the substituent can be protected in advance in accordance with a method described in Protective Groups in Organic Synthesis, Theodora W. Green (John Wiley & Sons), and the like, and the protecting group is removed at a desired stage.

A compound represented by the general formula (VIII) and a compound represented by the general formula (III-A) are dissolved in a solvent, such as N,N-dimethylformamide, tetrahydrofuran, acetonitrile, and the like. An N,N-dimethylformamide solution of a base, such as triethylamine, and the like, and dicyclohexylcarbodiimide (DCC), is added to that solution at −10 to 10° C., preferably in ice bath. 1-hydroxybenzotriazole may be added. The resultant solution is stirred at 10 to 50° C., preferably 20 to 30° C., for one hour to one day, preferably 5 to 10 hours, followed by typical subsequent processes. Thus, a compound represented by a general formula (IX) can be obtained.

Method A—Second Step

A deprotecting reaction can be carried out by a commonly used deprotecting reaction (Protective Groups in Organic Synthesis, Theodora W. Green (John Wiley & Sons)). For example, when $R^4$ is diphenylmethyl, a compound represented by a general formula (IX) can be added to anisole and trifluoro acetic acid at −10 to 10° C., preferably in ice bath. The mixture is stirred at the same temperature for 5 to 30 minutes, preferably 10 to 20 minutes. After the mixture is warmed to 20 to 40° C., the mixture can be stirred for 1 to 4 hours, preferably 2 to 3 hours.

The resultant deprotected substance can be reacted with a pyrrolidine derivative synthesized by a method described in Tetrahedron, 27, 2599 (1971) through a peptide bond formation similar to method A—first step, thereby obtaining a compound represented by the general formula (VI).

Method B—First Step

The amino group of 3-(4-thiazole)alanine synthesized in accordance with a method described in Synth. Commun., 20, 22, 3507 (1990) and Chem. Pharm. Bull., 38, 1, 103 (1990), is protected by a protecting group for an amino group, such as t-butyloxycarbonyl, benzyloxycarbonyl, 9-fluorenylmethoxycarbonyl, phthaloyl, trifluoroacetyl, and the like to obtain a compound represented by a general formula (X). This compound and a pyrrolidine derivative synthesized by a method described in Tetrahedron, 27, 2599 (1971) are subjected to a peptide bond formation.

When t-butyloxycarbonyl is used for the protection, the protecting reaction can be carried out as follows. 3-(4-thiazole)alanine is dissolved in a solvent, such as dioxane, tetrahydrofuran, acetonitrile, and the like. $Boc_2O$ is added to the solution at 0 to 50° C., preferably 10 to 30° C., and stirred for 1 to 5 hours, preferably 2 to 4 hours.

A peptide bond formation can be carried out in a manner similar to that of the above-described method A—First step.

Method B—Second Step

A deprotecting reaction for an amino group can be carried out as follows. When the protecting group is t-butyloxycarbonyl, a compound represented by a general formula (XI) is dissolved in a solvent, such as ethyl acetate, and the like. 1 to 4 N hydrochloric acid-ethyl acetate solution is added to that solution at −10 to 30° C., preferably in ice. The resultant mixture is stirred at the same temperature for 1 to 5 hours, preferably 2 to 3 hours.

The resultant deprotected substance can be subjected to a peptide bond formation similar to that of method A—First step, thereby obtaining a compound represented by the general formula (VI).

In the production method, a compound represented by the general formula (V-A) or (V-B) is preferably L-threonine or D-threonine($R^1$=methyl). Further, compounds represented by the general formulas (VII-A), (VII-B), (II-A), (II-B), (I-A), (I-B), (III-A), (III-B), (IV-A), (IV-B), and (VI) are also preferably compounds derived from L-threonine or D-threonine.

As $R^2$, benzyl is preferable. As $R^3$ and Y, methyl is preferable.

In Examples, the following abbreviations are used.

Me:methyl

Z:benzyloxycarbonyl

EXAMPLES

Example 1

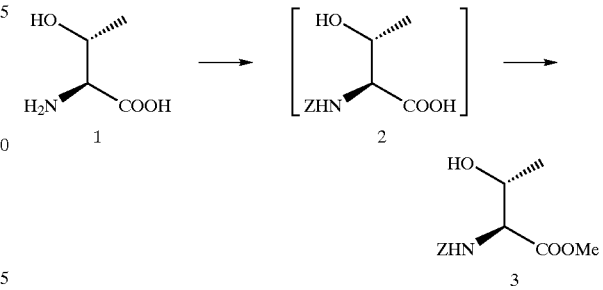

Potassium hydroxide (54.77 g) and a compound (1) (L-threonine) (100.0 g) were dissolved in water (1000 ml). To the solution was added potassium carbonate (139.23 g). The resultant solution was cooled below 10° C. Toluene (180 ml) solution of Z—Cl (157.5 g) was dropped into the solution at 10±5° C. for about one hour while the solution was vigorously stirred. The stirring was further continued for about 1.5 hours at the same temperature. Thereafter, the resulting reaction mixture was extracted with toluene (120 ml). The aqueous layer was washed with toluene (200 ml). Each toluene layer was extracted with water (50 ml) again. The aqueous layers were combined. To the resultant aqueous layer was added 25% hydrochloric acid (about 294 g) to adjust the pH to 2.0±0.5, followed by extraction with ethyl acetate (800 ml). The organic layer was washed with 10% brine (400 ml). Each aqueous layer was extracted with ethyl acetate (200 ml) again. Thereafter, the organic layers were combined. The organic layer was evaporated. Adding ethyl acetate (1000 ml) to the residue and condensing were repeated twice. Further, methanol (500 ml) was added, followed by evaporation. Thereafter methanol was added to adjust the volume to about 440 ml. To the resultant methanol solution of compound (2) was dropped thionyl chloride (109.9 g) at 10±10° C., followed by stirring at 20±10° C. for 2.5 hours. The reaction mixture was dropped into a slurry of sodium hydrogencarbonate (211.6 g) in water (1320 ml) over about 30 minutes. The resultant slurry was stirred at 5° C. for one hour. Thereafter, crystals were collected by filtration and dried, to obtain 206.3 g of compound (3) (yield 92%).

Melting point: 91° C.

$^1$H NMR (CD$_3$OD) δ1.19 (d, J=6.38, 3H), 3.73 (s, 3H), 4.21–4.31 (m, 2H), 5.11 (s, 2H), 7.30–7.38 (m, 5H)

Example 2

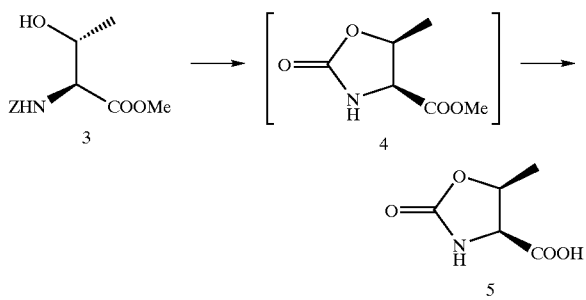

A solution of a compound (3) (50.0 g) and thionyl chloride (24.48 g) in toluene (250 ml) was stirred at 80° C. for 8 hours and thereafter was cooled to room temperature. The reaction mixture was extracted with water (150 ml). The aqueous layer was washed with toluene (25 ml). Each toluene layer was extracted with water (50 ml) again. Thereafter, the aqueous layers were combined. 36% hydrochloric acid (18.94 g) was added to the resultant aqueous layer. The aqueous layer was stirred at 80° C. for one hour and thereafter the water was evaporated. Water (100 ml) was added to the residue, followed by condensation. Adding acetonitrile (200 ml) to the residue and condensing were repeated three times. Acetonitrile was added to adjust the volume to about 50 ml. The resultant slurry was stirred at 0±5° C. for one hour. Thereafter, crystals were collected by filtration and dried. Thus, 17.4 g of compound (5) was obtained (yield 64%)).

Melting point: 165° C.

$^1$H NMR (CD$_3$OD) δ1.38 (d, J=6.52, 3H), 4.40 (d, J=8.64, 1H), 4.96 (dq, J=6.54, J=8.66, 1H) [α]$_D^{20}$–19.5° (C=1.0, H$_2$O)

Example 3

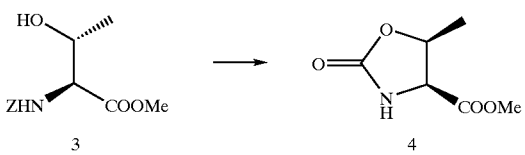

A solution of a compound (3) (3.0 g) and thionyl chloride (1.47 g) in toluene (15 ml) was stirred at 80° C. for 8 hours and thereafter was cooled to room temperature. The reaction mixture was extracted with water (9 ml). The aqueous layer was washed with toluene (1.5 ml). Each toluene layer was extracted with water (3 ml) and water (1.5 ml). The aqueous layers were combined. The resultant aqueous layer was condensed, thereby obtaining 1.48 g of compound (4) as oil (yield 83%).

$^1$H NMR (CD$_3$OD) δ1.31 (d, J=6.48, 3H), 3.79 (s, 3H), 4.46 (d, J=8.52, 1H), 4.96 (dq, J=6.48, J=8.52, 1H)

Example 4

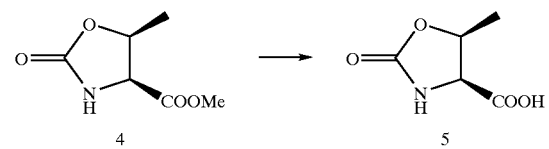

Methanol (5 ml) was added to compound (4) (1.0 g) and cooled in ice. 20% aqueous sodium hydroxide solution (2.5 g) was added to the solution, which was in turn stirred in ice bath for 30 minutes. 98% sulfuric acid (0.62 g) was added to the solution. Thereafter, precipitated crystals were filtered out and the filtrate was condensed. Adding acetonitrile (5 ml) to the residue and condensing were repeated four times. Acetonitrile (8 ml) was added to the resultant residue. The solution was dried over anhydrous sodium sulfate (2.2 g). The sodium sulfate was filtered out and the filtrate was condensed. The resultant slurry was stirred in ice bath for 30 minutes. Thereafter, crystals were collected by filtration and dried, thereby obtaining 0.50 g of compound (5) (yield 55%).

Example 5

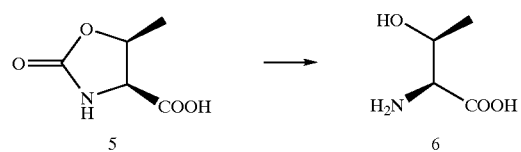

36% hydrochloric acid (10.5 g) was added to compound (5) (3.00 g). The solution was refluxed under stirring for 15 hours. Thereafter, water was evaporated and water (10 ml) was added to the residue, thereafter condensing. The residual oil matter was dissolved in water (10 ml). Aqueous lithium hydroxide solution was added to the solution to be adjusted to pH 6, followed by evaporation of water. Methanol (8 ml) was added to the resultant solid, followed by stirring at room temperature for one hour, thereafter subjected to filtration and dried. Thus, 2.25 g of compound (6) (L-allo-threonine) was obtained (yield 91%).

$^1$H NMR (D$_2$O) δ1.20 (d, J=6.30, 3H), 3.83 (d, J=3.90, 1H), 4.36 (dq, J=3.90, J=6.60, 1H)

[α]$_D^{20}$+9.07° (C=2.0, H$_2$O)

INDUSTRIAL APPLICABILITY

According to the production method of the present invention, oxo-oxazoline derivatives and allo amino acid derivatives can be produced in a stereoselective and inexpensive manner.

What is claimed is:

1. A method for production of a compound represented by the general formula (IV-A) or the general formula (IV-B), comprising the steps of:

obtaining a compound represented by general formula (I-A) or the general formula (I-B) by treating a compound represented by general formula (II-A) or general formula (II-B) with thionyl chloride as follows:

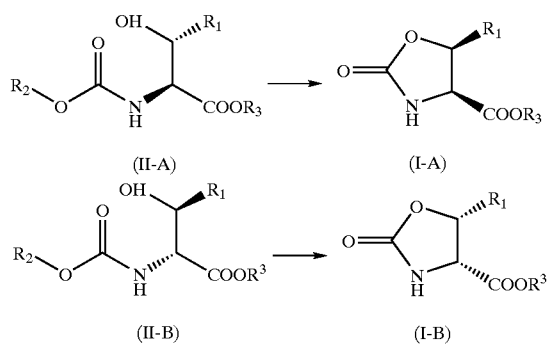

(II-A) → (I-A)

(II-B) → (I-B)

wherein $R^1$ is an optionally substituted lower alkyl, an optionally substituted aryl, an alkynyl, or an optionally substituted heteroaryl; $R^2$ is a lower alkyl, an optionally substituted aralkyl, or an optionally substituted heteroarylalkyl; and $R^3$ is a lower alkyl;

and subjecting the obtained compound represented by the general formula (I-A) or the general formula (I-B) to a hydrolysis as follows:

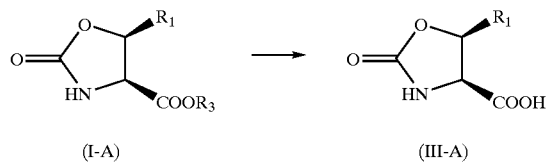

(I-A) → (III-A) or (I-B) → (III-B)

wherein $R^1$ and $R^3$ are as described above;

and then subjecting a compound represented by the general formula (III-A) or the general formula (III-B) to a hydrolysis as follows:

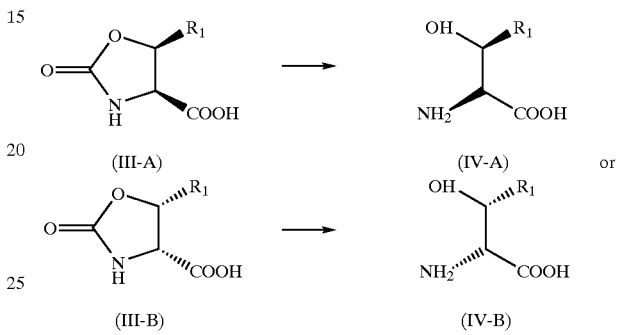

(III-A) → (IV-A) or (III-B) → (IV-B)

wherein $R^1$ is as described above.

* * * * *